United States Patent [19]

Kulbakh et al.

[11] 4,007,166
[45] Feb. 8, 1977

[54] MEGLUMINE COMPLEXES OF FUNGICIDAL POLYENE MACROLIDE ANTIBIOTICS AND METHOD OF PREPARING SAME

[76] Inventors: Valter Osvaldovich Kulbakh, Bukharestskaya ulitsa, 86, korpus 1, kv. 85; Tatyana Mikhailovna Kokushina, prospekt Metallistov, 16, kv. 66; Irina Kondratievna Lagert, Moskovskoe shosse, 16, kv. 163; Georgy Avxentievich Mikhailets, ulitsa Lanskaya, 10, kv. 100; Galina Vasilievna Kholodova, ulitsa B. Pushkinskaya, 40, kv. 9; Oleg Nikolaevich Ekzemplyarov, Suvorovsky prospekt, 22b, kv. 14; Ruvim Bentsionovich Zelmanov, ulitsa Chaitkovskogo, 13, kv. 20; Leonid Borisovich Sokolov, ulitsa Novorossiiskaya, 22, kv. 45; Evgeny Davidovich Etingov, ulitsa Zvezdnaya, 8, kv. 43; Irina Mikhailovna Lushitskaya, ulitsa Belgradskaya, 42, korpus 2, kv. 26, all of Leningrad, U.S.S.R.

[22] Filed: Apr. 24, 1974

[21] Appl. No.: 463,843

[52] U.S. Cl. .................................. 536/17; 424/180

[51] Int. Cl.$^2$ .......................................... C07H 5/04
[58] Field of Search ........................... 260/210 AB

[56] References Cited
OTHER PUBLICATIONS

Kittila, R. S., "DMF," EI Dupont de Nemours & Co. (Inc.) 1967, p. 33.
Pansy et al. "Comparative Chemotherap. Act of Heptaene Macrolide Antifungal Antibiotics" Journal of Antibiotics, vol. 25, No. 7 1972, pp. 405–408.

*Primary Examiner*—Lewis Gotts
*Assistant Examiner*—Cary Owens

[57] ABSTRACT

Meglumine complexes of fungicidal polyene macrolide antibiotics of the formula:

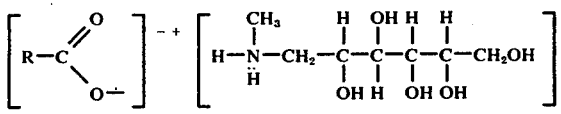

wherein R is the remainder of a fungicidal polyene macrolide antibiotic.

6 Claims, No Drawings

MEGLUMINE COMPLEXES OF FUNGICIDAL POLYENE MACROLIDE ANTIBIOTICS AND METHOD OF PREPARING SAME

The method of preparing said compounds involves interaction of a fungicidal polyene macrolide antibiotic of the formula RCOOH where R is the remainder of a fungicidal polyene macrolide antibiotic, with N-methyl-D-glucamine in a medium of dimethylsulphoxide, dimethylformamide or a mixture thereof at a temperature within the range of from 50° to 65° C with the formation of a reaction mixture and subsequent isolation of the desired product therefrom.

The medicated compounds containing as an active principle meglumine complexes of fungicidal polyene macrolide antibiotics possess fungicidal and protistocidal activity and may be useful in medicine for treating candidoses and aspergilloses, while meglumine complexes of amphotericin B and mycoheptine may be used, in addition, for treating most dangerous systemic mycoses by way of oral and inhalational administration as well as by instillation, and for treating leishmaniasis, schistosomiasis, lambliasis, and trichomoniasis.

The present invention relates to novel chemical compounds, viz. meglumine (N-methyl-D-glucamine) complexes of fungicidal polyene antibiotics, methods of preparing same, and medicated compounds based on said meglumine complexes.

Said compounds according to the present invention have the following generic formula:

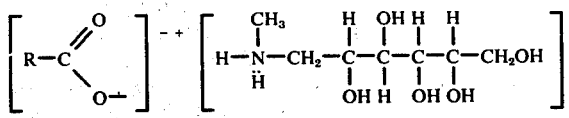

wherein R is the remainder of a fungicidal polyene macrolide antibiotic.

Said novel compounds comprise solid hygroscopic substances in the form of yellow amorphous powders soluble in water, dimethylsulphoxide, sparingly soluble in dimethylformamide, practically insoluble in diethyl ether, acetone and mixtures thereof, and only slightly soluble in chloroform and ethanol.

Said substances possess a fungicidal and protistocidal activity and may be useful in medicine as medicated compounds for treating condidoses and aspergilloses, while some of them may be used for treating most dangerous systemic mycoses, leishmaniasis, schistosomiasis, lamblisis, trichomoniasis, and prostate hypertrophy.

Known in the art are medicated compounds for treating said diseases such as polyene macrolide antibiotics especially those prepared from biolgically suitable and physiologically permissible tetraenes such as nystatine, pimaricin, and heptaenes of the non-aromatic sub-group such as candidine, amphotericin B, mycoheptine, and those of the aromatic sub-group such as levorine, candicydine, trichomycin, gamicin, sodium salts thereof and complexes with sodium desoxycholeate.

These medicated compounds, however, feature some essential disadvantages.

The starting fungicidal polyene macrolide antibiotics per se are known to be practically insoluble in water, wherefore, even with a great specific surface area of finely divided particles, they are difficult to absorb from alimentary tract when administered orally and are insufficiently effective against a generalized fungal infection. Thus, amphotericin B is totally ineffective for systemic mycoses when orally administered to persons, notwithstanding the chemotherapeutic effect produced on animals which may be presumably attributed to different pH values of gastric juice: near to neutral for mice and about pH = 2–3 for human beings, contributing to inactivation due to opening of the lactone ring of amphotericinolamide and due to the presence of a hemiketal group between $C_{13}$ and $C_{17}$ of the macrolactone ring causing insolubility of amphotericin B.

Sodium salts of fungicidal polyene macrolide antibiotics, though featuring advantages of water-solubility and decreased surface tension of their aqueous solutions, whereby the range of application thereof is widened for treating candidoses and aspergilloses of nasopharynx, respiratory tract and lungs by inhalation administration, as well as for treating candidosous vulvovaginitis, cystitis, colpitis, and ureteritis by way of instillation, have, nevertheless, an essential disadvantage of reducing biological activity during the preparation by way of reacting labile polyene antibiotics with strongly basic compounds and during storage due to the opening of the lactone ring of a polyene macrolide-antibiotic.

The complex of amphotericin B with sodium desoxycholeate is not suitable for oral administration due to its local irritation effect upon the alimentary tract caused by desoxycholeic acid and is employed for in inhalation administration in the form of an aerosol only as an option, since it has an undesirable side-effect residing in paresis of ciliated epithelium. Essential disadvantages of this complex also reside in an increased pyrogenic effect, nephrotoxicity and general toxicity even within the range of progressively increased therapeutic doses of amphotericin B of from 0.25 to 1.5 mg/kg when administered by an intravenous instillation; these disadvantages make this medicated compound an optional one above-mentioned complicated and situational procedure of its administration makes it applicable only in stationary hospitals.

Known in the art are methods of preparing water-soluble fungicidal polyene macrolide antibiotics by way of treating of a solution or suspension thereof in an organic or aquo-organic solvent such as methanol, aqueous acetone or dimethylformamide, with solutions of sodium methylate or butylate, caustic soda or sodium desoxycholeate.

Essential disadvantages of such a treatment of solutions of labile polyene macrolide antibiotics with said strongly basic compounds reside in reducing the yield of the thus-obtained antibiotic substances and biological activity thereof which is related to a side inactivation reaction due to the opening of the lactone ring of a polyene macrolide antibiotic.

Therefore, it has been hitherto impossible to obtain, by chemical transformation of fungicidal polyene macrolide antibiotics, medicated compounds for treating mycoses, especially most dangerous systemic mycoses, which compounds could be effective both at an oral and inhalational administration.

We were the first to prepare meglumine complexes of fungicidal macrolide antibiotics of the formula:

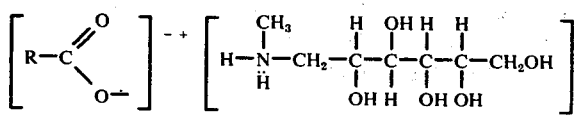 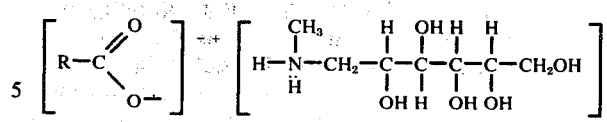

wherein R is the remainder of a fungicidal polyene macrolide antibiotic.

The method of preparing meglumine complexes of fungicidal polyene macrolide antibiotic according to the present invention resides in reacting of a fungicidal polyene macrolide antibiotics of the formula RCOOH, where R is the remainder of a fungicidal polyene macrolide antibiotic, with N-methyl-D-glucamine in a medium of dimethylsulphoxide, dimethylformamide or a mixture thereof at a temperature within the range of from 50° to 65° C to yield a reaction mass, followed by isolation of the desired product therefrom.

To isolate the desired product from the reaction mass, it is advisable to separate impurities by filtration and to add a 6–7-fold volume of a mixture of diethyl ether with acetone in a ratio of from 1:1 to 3:7 by volume to the filtrate, to the filter off the precipitate, to wash it with acetone or with a mixture of acetone with diethyl ether and to dry at 20° C and under a residual pressure of 10 mm Hg at most.

The aminoalcohol-meglumine [1-deoxy-1-(methylamino)glucitol] or N-methyl-D-glucamine comprises a biologically suitable and physiologically permissible substance forming, as it has been unexpectedly first discovered by the inventors, water-soluble complexes with fungicidal polyene macrolide antibiotics substantially widening the range of their application in medical practice.

Meglumine may be used as it is and in the form of an aqueous solution with a concentration of from 0.25 to 1 g/ml with an excess of up to 5 moles per 1 mole of a fungicidal polyene macrolide antibiotic for a better solubilization of the resulting complex.

As fungicidal polyene macrolide antibiotics, reacted with meglumine may be all substances capable of complexing and containing a free carboxyl group; however, use is preferably made of those employed in medicine selected from the group of tetraenes such as nystatine, pimaricin and the like; as well as from heptanenes of the non-aromatic sub-group such as amphotericin B, mycoheptine, candidine and the like, and from those of the aromatic sub-group such as levorine, trichomicin, gamicin and the like.

The formation of said complexes with meglumine has resulted in an essential improvement of pharmacological properties of the starting insoluble fungicidal polyene macrolide antibiotics. The meglumine complexes prepared in accordance with the present invention posses, as compared to the starting insoluble antibiotics, novel pharmacological properties, namely: solubility in water, much better absorption from the alimentary tract when administered orally, and therewith, quite unexpected better tolerance and lower nephrotoxicity as compared, for example, to amphotericin B.

The yield meglumine complexes of fungicidal polyene macrolide antibiotics ranges from 85 to 96% based on the activity of the starting antibiotics.

Meglumine complexes of fungicidal polyene macrolide antibiotics of the formula:

wherein R is the remainder of a fungicidal polyene macrolide antibiotic comprise an active principle of medicated compounds which may be useful in the treatment of fungal diseases: candidoses, aspergilloses of various localization and, which is most important, some of them unexpectedly turned to be highly effective and still non-toxic when administered orally for the treatment of most dangerous systemic mycoses: coccidiosis, histoplasmosis, cryptococcosis, North-American blastomycosis, sporotrichlosis, mould mycoses, chromomycosis, chronic forms of granulomatous and disseminated candidosis, as well as for treating protozoa-caused diseases.

These medicated compounds are referred to as follows:

1. Meglumine complex of amphotericin B - amphoglucamine
2. Meglumine complex of mycoheptine - mycoglucamine;
3. Meglumine complex of levorine - levoriglumine;
4. Meglumine complex of nystatine - nystaglumine.

These medicated compounds may be administered in the form of encapsulated powder or in the form of tablets with pharmaceutically suitable filler, or in the form of aqueous solutions prepared extemporaneously from a sterile powder for inhalational administration in the case of mycoses of mouth cavity, nasopharynx, respiratory tract, and lungs, as well for administration by insillation in the case of candidosis vulvovaginistis, colpitis, cystitis, and ureteritis.

Amphoglucamine absorbed when administered orally, has been unexpectedly found non-toxic in experiments on animals at this mode of administration. Its tolerable dose for oral administration to white mice is 2,000 mg/kg. Specific biological activity of amphoglucamine determined by the diffusion-into-agar method with the test microbe Candida utilis LIA-TO37 is at least 250 mcg/mg (ED/mg) as compared to the international standard amphotericin B. Maximal tolerable dose of amphoglucamine when administered intravenously is 7.5 to 15 ED/mouse.

When orally administered to mice one day after intravenous infection with fatal doses of Candida Albicans 13 and Coccidioides Unitis 158 respectively pathogenetic organisms of candidosis and coccidiocidosis once a day for a period of 10 days in doses of 2,535 and 4,750 mcg/kg (ED/kg) respectively of an aqueous amphoglucamine solution, all treated mice were alive without any specific lesions of viscera whereas all control infected mice receiving no medicated compound were dead. When administered by inhalation in the concentration of 5,000 mcg/kg (ED/kg) for a period of 5 to 7 days at the same infections, a 100% survival of treated animals was reached, while all control animals were dead.

The growth of the majority of pathogenic fungi is suppressed by amphoglucamine in vitro in a concentration within the range of from 0.5 to 6.25 mcg/ml, wherefore amphoglucamine may be used for oral treatment of most dangerous deep mycoses, namely: coccidioidosis, histoplasmosis, cryptococcosis, sporotrichosis, North-American blastomycosis, chromomycosis, mould mycoses, visceral candidoses, chronic forms of granulomatous and disseminated candidosis, as well as candidosis of alimentary tract and enteral candida-carrier state.

Tetratogenic action of amphoglucamine has been studied in tests on 136 pregnant rats of the Vischar line.

In acute experiments with doses of 100 and 1,000 mg/kg, amphoglucamine exerts a pronounced toxic effect which is manifested in interruption of pregnancy. When administered in doses of 20 mg/kg, amphoglucamine reveals no fetus development defects. Therefore, amphoglucamine has no teratogenic action.

When administered in doses of 50 mg/kg, amphoglucamine ensured sanitation of 74% of the animals in respect of lamblia and 88% — in respect of trichomonia. In doses of 25 mg/kg in the case of lambliasis, mycoglucamine cured 40% of the animals and 90% in the case of trichomoniasis.

Mycoglucamine has been tested in the oral treatment of generalized condidosis when administered once a day during 10 days in doses of 50, 100, 250, and 500 mcg/kg (ED/kg). $ED_{50}[(ED/kg) \times 10)]$ on the day of the control animals death was 70 to 130 12 days after and 21 days after it was 240 to 270; 28 days after it was 400 to 530. Mycoglucamine was also active in the intravenous treatment of generalized candidosis. $ED_{50}$ on the day of all the control animals death was 37 ED/kg, three weeks after it was 50 ED/kg, and 5 weeks after it was 62 ED/kg. Mycoglucamine has a therapeutic effect similar to that of a finely divided powder of mycoheptine when administered orally, but it widens the range of the antibiotic application by way of inhalation and instillation.

Lavoriglumine appeared to be effective in the case of generalized candidosis when administered intravenously.

Nystaglumine was as effective as a sodium salt of nystatine when administered intravenously to white mice during 7 days in doses of 2,000 and 2,800 ED/kg respectively after intravenous infection with the fatal dose of *Candida albicanis* 13, while all the control animals were dead.

On the basis of experimental data and clinical studies it is recommended that amphoglucamine be orally administered in the form of a powder, capsules or tablets containing 100 mg (100,000 ED) of the active principle twice a day after meals in single doses of from 200 to 500 mg (200,000 to 500,000 ED) for adults, and for children: up to 2 years old - 25 mg (25,000 ED, a quarter of a tablet); 2 to 6 years old - 100 mg (100,000 ED - one tablet); 6 to 9 years old - 150 mg (150,000 ED - a tablet and a half); 9 to 14 years - 200 mg (200,000 ED - two tablets); 14 years and older - as for adults for a period of 10 to 14 days, and up to 3–4 weeks in chronic cases. Treating course may be repeated in 5–7 days.

Amphoglucamine may be also used for treating condidoses and aspergilloses of mouth cavity, nasopharynx, respiratory tract and lungs when administered by inhalation in the form of an aerosol, extemporaneously prepared aqueous solution of amphoglucamine once or twice a day in a single dose of 10 to 56 mg (10,000 to 56,000 ED) to adults in 5–10 ml for a period of 10–12 days, as well as in the form of installations and enemae.

Since amphoglucamine is active in respect of protozoa, viz. lamblia and trichomonia, while amphotericin B proper is active against leishmania and schistosomia, amphoglucamine may be used for treating lambliasis, trichomoniasis, leishmaniasis, and schistosomiasis as well using the same administration techniques.

Mycoglucamine may be also used in single doses of from 10 to 56 mg once or twice a day to adults for treating candidoses and aspergilloses of lungs by inhalation of an aerosol as well as for treating candidosous cystites, uretreitis, vulvovaginitis, colpitis, and trichomoniasis by instillation of an aqueous solution.

Levoriglumine may be used in doses of 150,000 to 200,000 ED and nystaglumine — in doses of 150,000 ED a day in a 5–10 ml volume when administered orally and rectally for treating candidoses of alimentary tract and viscera, enteral candida-carrier state, as well as in the form of an aqueous aerosol for administration by inhalation or gargle in the case of treating candidoses and aspergilloses of mouth cavity and nasopharynx, respiratory tract and lungs.

Due to effectiveness of polyene macrolide antibiotics especially of amphotericin B (fungisone) in the case of prostate hypertrophy (cf. C. Jamamote et al., The Nippon University Journal of Medicine, 1971, 13, 291–304) in a dose ranging from 800 to 1,200 mg a day four times a day in a single dose of 200 to 300 mg for a period of 2 to 10 weeks, and due to effectiveness of levorine in a day dose of 2,000,000 ED four times a day at a single dose of 50,000 ED (cf. G. A. Mickhailetz et al. Voprosy onkologii, 1971, 5), amphoglucamine and levoriglumine may be administered at a lesser dose as compared to the starting insoluble and, hence, difficult-to-absorb antibiotics for treating prostate adenoma.

Shelf-life of meglumine complexes of fungicidal polyene macrolide antibiotics stored in a dry, light-tight place, hermetically-sealed, at a temperature of +4° C is one year (observation period).

Meglumine complexes of fungicidal polyene macrolide antibiotics are produced in the form of powders, capsules and tablets with pharmaceutically suitable fillers such as lactose, glucose, as well as in the form of sterile powders for per os administration.

Contraindications are individual tolerance and pronounced renal diseases accompanied by misaction thereof; in the case of meglumine complexes of the aromatic sub-group heptaenes administered per os the only contraindication is pregnancy.

Positive result of using fungicidal polyene macrolide antibiotics as compared to the original insoluble polyene antibiotics and their colloidal complexes with sodium desoxycholeate resides, first of all, in the possibility of orally treating generalized fungal infection due to a better absorption of meglumine complexes of polyene antibiotics from alimentary tract, better tolerance, reduced general and nephro-toxicuty as compared, for example, with a complex of amphotericin B with sodium desoxycholeate. This makes it possible to perform the treatment not in a stationary state by way of an instillational intravenous administration at a continuous control of a residual nitrogen in blood, but under ambulatory conditions including treatment of children; in appropriate cases the treatment may be performed by way of inhalational and intracavitary administration. A positive effect, as compared to the original insoluble antibiotics, also resides in a decreased dose for oral administration, for example in the case of amphoglucamine of 400 to 1,000 mg a day instead of 800 to 1,200 mg a day for amphotericin B (fungisone), which considerably lowers frequency and level of side effects of the antibiotic in addition to reduced treatment costs.

The method of preparing meglumine complexes of fungicidal polyene macrolide antibiotics is preferably embodied in the following manner.

A fungicidal polyene macrolide antibiotic selected from predominantly employed groups of tetraenes, heptaenes of the aromatic and non-aromatic subgroups is dissolved under stirring in a required amount of dimethylsulphoxide, dimethylformamide or a mixture thereof, heated to a temperature of 50° to 65° C and added, still under continuous stirring, with the calculated amount of meglumine or its aqueous solution with a concentration within the range of from 0.25 to 1 g/ml or in excess of up 5 moles per 1 mole of the fungicidal polyene macrolide antibiotic. Insoluble impurities are filtered off. The desired product, viz. meglumine complex of the fungicidal polyene macrolide antibiotic is precipitated from a clear filtrate by adding a 6–7-fold volume of a mixture of diethyl ether with acetone (in a volumetric ratio of from 1:1 to 3:7). The resulting precipitate is filtered off, washed with a mixture of diethyl ether with acetone or with individual acetone and dried at 20° C in vacuum, due to hygroscopicity of the compounds, under a residual pressure of 10 mm Hg at most.

A water-soluble meglumine complex of the fungicidal polyene macrolide antibiotic is obtained with a yield of from 85 to 96% based on the activity of the starting antibiotic.

To prepare a sterile powder, the meglumine complex of the fungicidal polyene macrolide antibiotic is dissolved in water; the solution is filtered through a bacterial filter aid "Millipore," bottled under aseptic conditions into flasks, frozen to a temperature of −40° C and dried by sublimation, whereafter the flasks with the sterile powder are hermetically sealed by means of rubber plugs and rolled up by means of aluminium caps.

For better understanding of the present invention some specific Examples are given hereinbelow.

EXAMPLE 1

Preparation of amphoglucamine 15 g of amphotericin B with a specific biological activity of 750 mcg/mg (ED/mg) are dissolved under stirring in 150 ml of dimethylsulphoxide upon heating to a temperature within the range of from 50° to 65° C and 15 ml of an aqueous solution of meglumine with a concentration of 1 g/ml are added thereto.

Meglumine [1-deoxy-1-(methylamino)-glucitol] $C_7H_{17}NO_5$ is used of a pharmacopeia purity grade according to U.S. Pharmacopeia, XVIII edition, page 291 with the basic substance content of at least 99%, melting point 128°–132° C (within the range of 2° C), specific rotation index $[\alpha]_{20°C}^D - 15.5°-17.5°$.

Insoluble impurities are filtered off. The resulting clarified filtrate is added with a 7-fold volume of a mixture of diethyl ether and acetone (in a volumetric ratio of 3:7 respectively). The resulting precipitate is filtered off washed with acetone, and dried at 20° C under a residual pressure of 10 mm Hg at most to give 22.36 g of amphoglucamine with a specific biological activity of 440 mcg/mg (ED/mg) according to the international standard for amphotericin B, which corresponds to the yield of amphoglucamine of 91.3% based on the activity of the starting amphotericin B. Meglumine complex of amphotericin B, viz. amphoglucamine with the brutto-formula $C_{54}H_{90}N_2O_{22}$ and molecular weight of 1192.3 is formed according to the scheme:

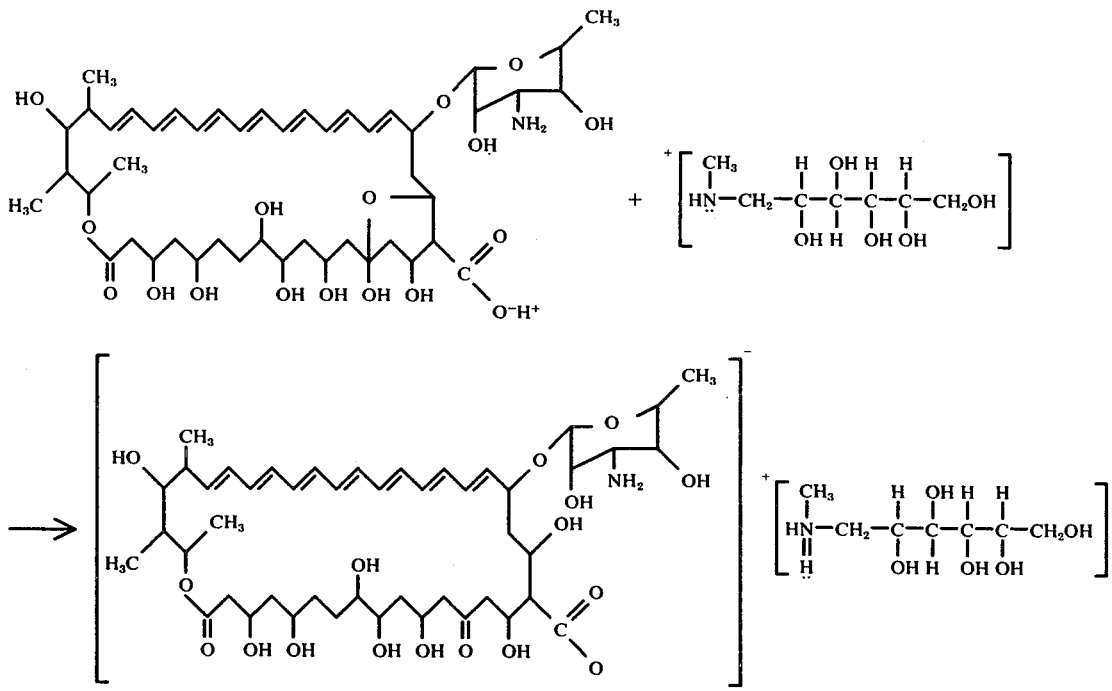

with the above-mentioned structural formula; it contains an excess of up to 3 moles of meglumine as a solubilizer. Amphoglucamine solubility in water is 100 mg/ml. Authenticity of amphoglucamine is identified by determining a distribution coefficient value $K_p = 3\text{-}3.8$ in the Borovsky system: methanol-chloroform-borate buffer with pH = 8.2 (2:2:1), specific absorption (extinction $E_{1cm}^{1\%}$) values at wave lengths of 363 ± 2, 383 ± 2, 406 ± 2 nm of at least 390, 660, 700 respectively calculated on the dry substance and by performing the silver amalgam reaction on N-methyl-d-glucosamine. Weight loss upon drying of amphoglucamine is 5% at most.

glucamine with the brutto-formula $C_{54}H_{88}N_2O_{22}$ is formed according to the equation:

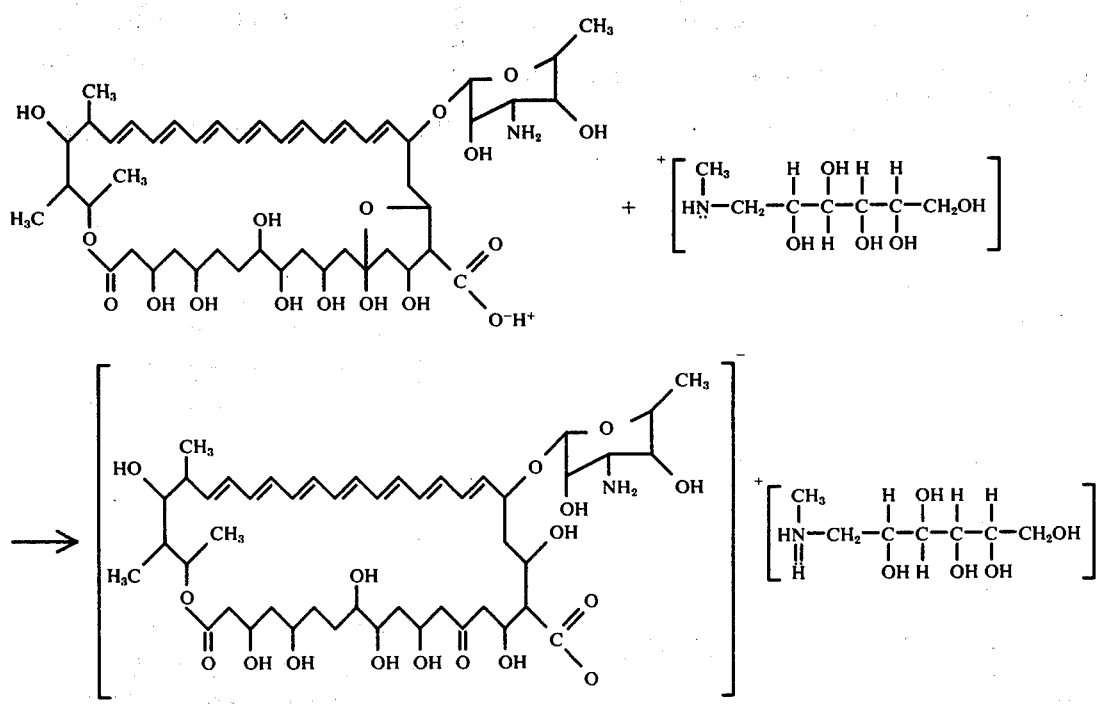

EXAMPLE 2

Preparation of amphoglucamine 19.7 g of amphotericin B with a specific biological activity of 750 mcg/mg (ED/mg) and 14.7 g of meglumine with the content of 1-deoxy-1-(methylamino)-glucitol of at least 99% are dissolved in 100 ml of dimethylsulphoxide at a temperature within the range of from 50° to 60° C and stirred for 10 minutes. The resulting solution is added with a 7-fold volume of a mixture of acetone with diethyl ether (in a volumetric ratio of 1:1). The precipitate is filtered off, washed with the same mixture of acetone with diethyl ether, and dried at 20° C under a residual pressure of 100 mm Hg to give 32.7 g of amphoglucamine with a specific biological activity of 440 mcg/mg (ED/mg) which corresponds to the yield of 96% of amphoglucamine based on the activity of the starting amphotericin B.

EXAMPLE 3

Preparation of mycoglucamine 7 g of mycoheptine with a specific biological activity of 450 mcg/mg according to the stardard for mycoheptine and 7 g of meglumine are dissolved in 40 ml of dimethylform amide at a temperature within the range of from 50° to 60° C under stirring for 10 minutes. The resulting transparent solution is added with a 7-fold volume of acetone. The precipitate thus formed is filtered off, washed with acetone, and dried at 20° C and under a residual pressure of 10 mm Hg to give 13.2 of mycoglucamine with a specific biological activity of 212 mcg/mg according to the standard for mycoheptine which corresponds to the yield of mycoglucamine of 89% based on the activity of the starting mycoheptine. The meglumine complex of mycoheptine-myco- II. Preparation of meglumine complexes of fungicidal polyene antibiotics - macrolides from heptaenes of the aromatic sub-group

EXAMPLE 4

Preparation of levoriglumine 3 g of levorine with a specific biological activity of 39,200 ED/mg are dissolved under stirring in 50 ml of dimethylformamide, heated to a temperature within the range of from 50° to 55° C and added, still under stirring, with 3.5 g of N-methyl-D-glucamine Insoluble impurities are filtered off and the clear filtrate is added with a 7-fold volume of a mixture of diethyl ether with acetone (in a volumetric ratio of 3:7). The resulting precipitate is filtered off, washed with the same mixture of acetone with diethyl ether and dried at 20° C and under a residual pressure of at most 10 mm Hg to give 4.2 of levoriglumine soluble in water in a concentration of 50 mg/ml with an extinction value $E_{1cm}^{1\%} = 520-560$ (80% ethanol), specific biological activity of 24,000 ED/mg according to the standard for levorine which corresponds to the yield of 85.7% based on the activity of the starting antibiotic.

Half-value fatal dose for white mice at intravenous administration $LD_{50} = 3.2$ mg/kg, while for a sodium salt of levorine $LD_{50} = 1.6 \pm 0.09$ mg/kg at the same mode of administration.

Structural formula of levorine and, hence, levoriglumine has not been completely established yet.

III. Preparation of a meglumine complex of fungicidal polyene antibiotic from the group of tetraenes

EXAMPLE 5

Preparation of nystaglumine 1 g of nystatine with a specific biological activity of 3,500 ED/mg are dissolved under stirring in 8 ml of dimethylformamide upon heating to a temperature within the range of from 50° to 55° C and added, still under stirring, with 1 ml of an aqueous solution of N-methyl-D-glucamine with the concentration of 0.255 g/ml.

As a result of reacting nystatine with meglumine, hystaglumine with the brutto-formula $C_{54}H_{92}N_2O_{22}$ is formed according to the scheme:

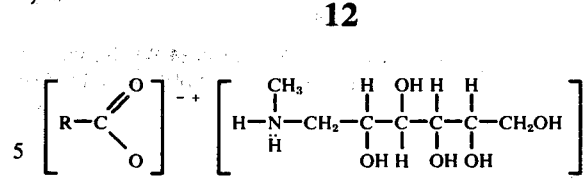

wherein R is the remainder of a fungicidal polyene

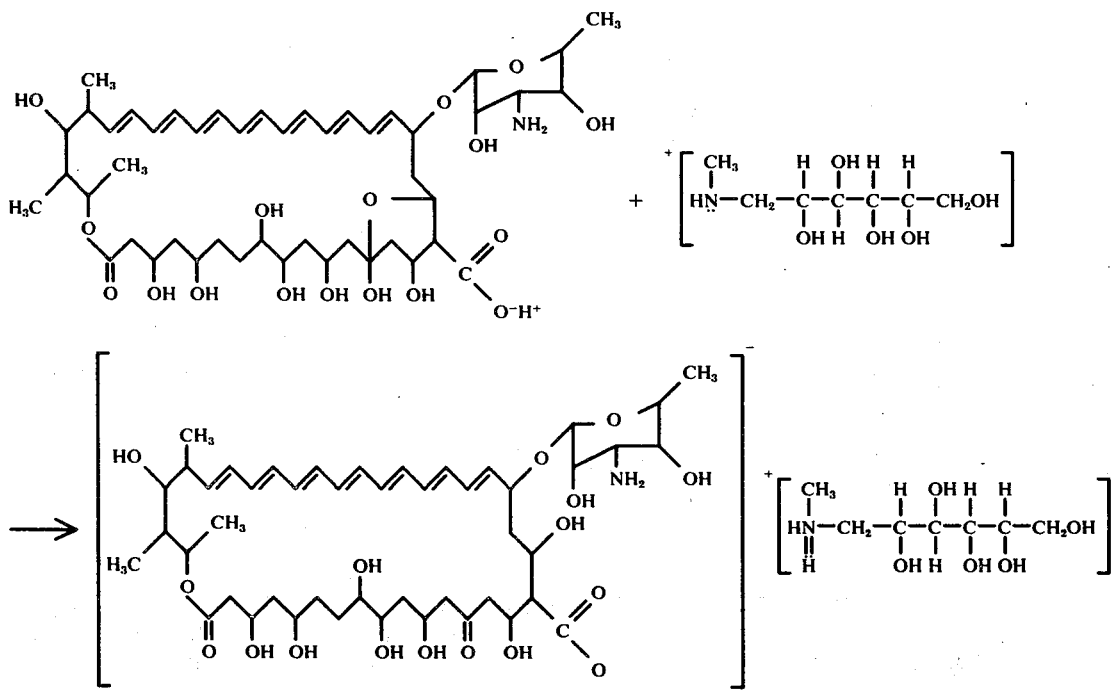

Possible impurities are filtered off. The clarified filtrate is added under stirring with a 6-fold volume of a mixture of diethyl ether with acetone (in a volumetric ratio of 3:7) to precipitate nystaglumine. The resulting precipitate is filtered off, washed with a mixture of acetone with diethyl ether (in a volumetric ratio of 1:1) and dried at 20° C and under a residual pressure of at most 10 mm Hg to give 1.05 g of nystaglumine soluble in water with a specific biological activity of 3,000 ED/mg which corresponds to the yield of 90% based on the activity of the starting antibiotic.

What is claimed is:

1. Meglumine complexes of fungicidal polyene macrolide antibiotics of the formula: macrolide antibiotic having no carboxyl groups, selected from the group consisting of tetraene antibiotics and non-aromatic heptaene antibiotics.

2. Meglumine complexes of fungicidal polyene macrolide antibiotics are claimed in claim 1, wherein said antibiotics are selected from the group consisting of nystatine, amphotericin B, mycoheptine, and levorine.

3. A compound according to claim 1 wherein said compound is amphoglucamine.

4. A compound according to claim 3 wherein said compound is mycoglucamine.

5. A compound according to claim 3 wherein said compound is levoriglumine.

6. A compound according to claim 3 wherein said compound is nystaglumine.

* * * * *

UNITED STATES PATENT AND TRADEMARK OFFICE
CERTIFICATE OF CORRECTION

PATENT NO. : 4,007,166  
DATED : February 8, 1977  
INVENTOR(S) : KULBAKH ET AL

It is certified that error appears in the above-identified patent and that said Letters Patent are hereby corrected as shown below:

Please amend as follows:

Column 1, line 19, change "mycoheptine" to --mycoheptin--
          line 51, change "lamblisis" to --lambliasis--
          line 55, change "biolgically" to --biologically--
          line 56, change "nystatine" to --nystatin--
          line 58, change "candidine" to --candidin--
          line 59, change "tine" to --tin--
          line 60, change "rine" to --rin--; change "candicydine" to --candicidin--;

line 66, change "wherefore" to --therefore--
Column 2, line 10, change "amphotericinolamide" to --amphotericinolide--
          line 31, cancel "in"
Column 3, line 45, after "medicine" insert --and--
          line 46, change "nystatine" to --nystatin--
          line 47, change "heptanenes" to --heptaenes--
          line 49, change "mycoheptine, candidine" to --mycoheptin, candidin--
          line 50, change "levorine, trichomicin" to --levorin, trichomycin--

UNITED STATES PATENT AND TRADEMARK OFFICE
CERTIFICATE OF CORRECTION

PATENT NO. : 4,007,166                          Page 2 of 6
DATED : February 8, 1977
INVENTOR(S) : KULBAKH ET AL It is certified that error appears in the above-identified patent and that said Letters Patent are hereby corrected as shown below:

```
Column 4, line 16, change "iosis" to --ioidosis--
         line 25, change "mycoheptine" to --mycoheptin--
         line 27, change "levorine" to --levorin--
         line 28, change "nystatine" to --nystatin--
         line 36, change "insillation" to --instillation--
         lines 45 and 48, change "ED" to --iu--
         line 50, change "fatal" to --lethal--
         line 51, change "Unitis" to --immitis--
         line 52, change "coccidiocidosis" to
                 --coccidioidosis--
         lines 54 and 59, change "ED" to --iu--
         line 66, change "wherefore" to --therefore--
Column 5, line 7,  change "Vischar" to --Visthar--
         lines 23, 28, 29 and 30, change "ED" to --iu--
         line 32, change "tine" to --tin--
         line 40, change "ED" to --iu--
         line 41, change "fatal" to --lethal--
         line 42, change "albicanis" to --albicans--
         lines 47, 49 to 52, 54 and 64, change "ED" to --iu--
```

UNITED STATES PATENT AND TRADEMARK OFFICE
CERTIFICATE OF CORRECTION

PATENT NO. : 4,007,166
DATED : February 8, 1977
INVENTOR(S) : KULBAKH ET AL.

It is certified that error appears in the above—identified patent and that said Letters Patent are hereby corrected as shown below:

Column 6, line 11, change "ED" to -- iu --
         line 21, change "Jamamote" to -- Yamamote --
         lines 26 and 27, change "ED" to -- iu --
Column 8, lines 5 and 23, change "ED" to -- iu --
Change the lower right-hand part of the formula above line 59 to read as follows:

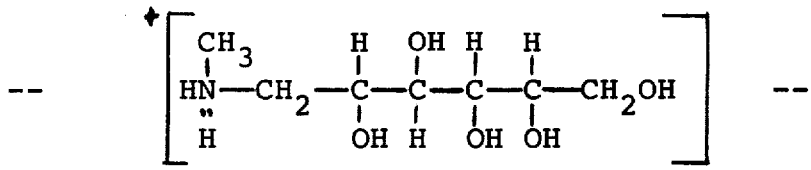

Column 8, line 64 change "Boroysky" to -- Borowski --

Column 9, change formulas to read as follows:

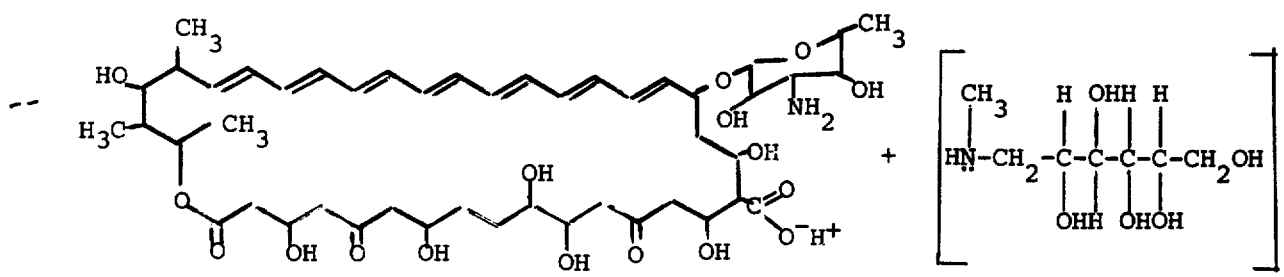

UNITED STATES PATENT AND TRADEMARK OFFICE
CERTIFICATE OF CORRECTION

PATENT NO. : 4,007,166           Page 4 of 6
DATED      : February 8, 1977
INVENTOR(S): KULBAKH ET AL.

It is certified that error appears in the above-identified patent and that said Letters Patent are hereby corrected as shown below:

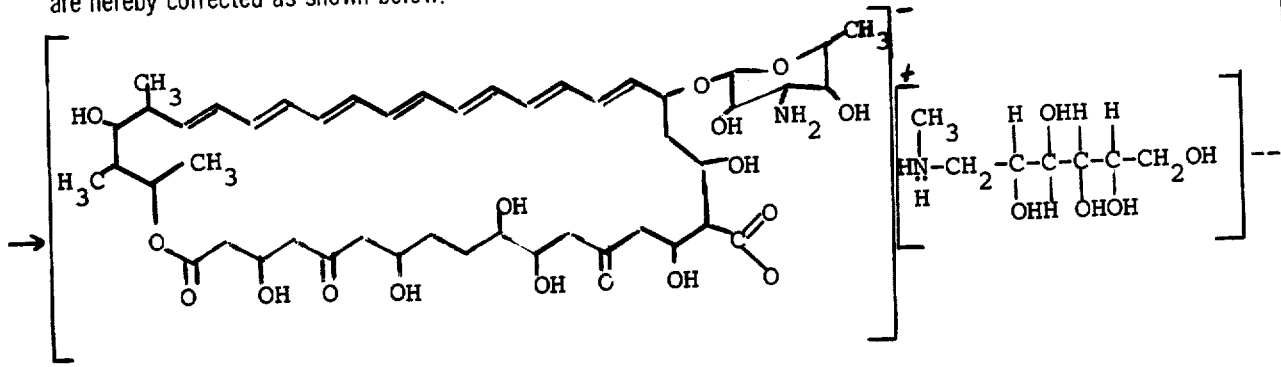

Column 9, lines 37 and 48, change "ED" to -- iu --
         line 55, change "mycoheptine" to -- mycoheptin --
         line 57, change "tine" to -- tin --
         line 66, change "tine" to -- tin --
         line 68, change "tine" to -- tin --; change
                  "mycoheptine" to -- mycoheptin --
Column 10, line 38, change "levorine" to -- levorin --
          line 39, change "ED" to -- iu --
          line 49, change "4.2" to -- 4.2 g --
          line 52, change "ED" to -- iu --
          line 55, change "fatal" to -- lethal --
          lines 57 and 59, change "levorine" to -- levorin --
          line 67, change "nystatine" to -- nystatin --
          line 68, change "ED" to -- iu --

UNITED STATES PATENT AND TRADEMARK OFFICE
CERTIFICATE OF CORRECTION

PATENT NO. : 4,007,166
DATED : February 8, 1977
INVENTOR(S) : KULBAKH ET AL.

It is certified that error appears in the above-identified patent and that said Letters Patent are hereby corrected as shown below:

Column 11, change formulas to read as follows:

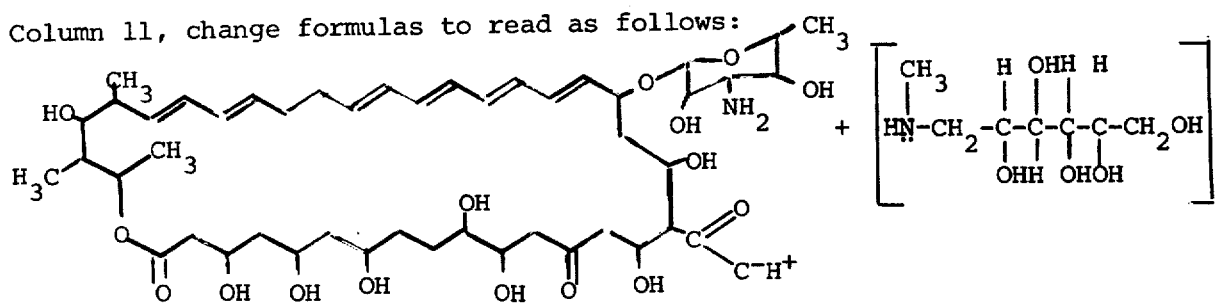

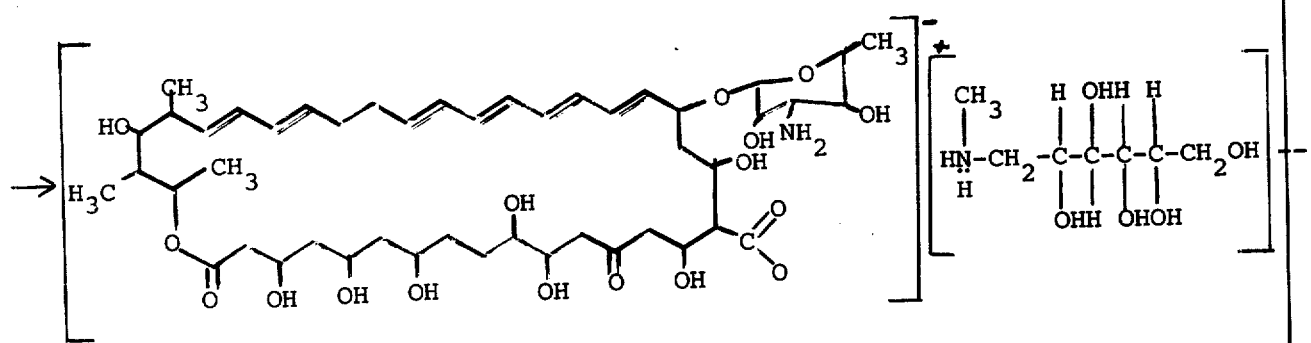

UNITED STATES PATENT AND TRADEMARK OFFICE
CERTIFICATE OF CORRECTION

PATENT NO. : 4,007,166

DATED : February 8, 1977

INVENTOR(S) : KULBAKH ET AL.

It is certified that error appears in the above-identified patent and that said Letters Patent are hereby corrected as shown below:

Column 11, line 48, change "ED" to -- iu --

Column 12, line 39, after "aromatic" insert -- and aromatic subgroups of -- line 43, change "nystatine, mycoheptine and levorine" to -- nystatin, mycoheptin and levorin --.

Signed and Sealed this

Twenty-second Day of May 1979

[SEAL]

Attest:

RUTH C. MASON
Attesting Officer

DONALD W. BANNER
Commissioner of Patents and Trademarks